United States Patent [19]
Wilton

[11] Patent Number: 5,449,607
[45] Date of Patent: Sep. 12, 1995

[54] ASSAY FOR THE QUANTITATIVE DETERMINATION OF SUBSTRATES CAPABLE OF UNDERGOING ENZYMATIC HYDROLYSIS TO RELEASE LONG-CHAIN FATTY ACIDS

[75] Inventor: David C. Wilton, Bassett, England

[73] Assignee: British Technology Group Limited, London, England

[21] Appl. No.: 107,702

[22] PCT Filed: Mar. 16, 1992

[86] PCT No.: PCT/GB92/00461

§ 371 Date: Aug. 18, 1993

§ 102(e) Date: Aug. 18, 1993

[87] PCT Pub. No.: WO92/16847

PCT Pub. Date: Oct. 1, 1992

[30] Foreign Application Priority Data

Mar. 18, 1991 [GB] United Kingdom ............ 9105707

[51] Int. Cl.⁶ ............ G01N 33/50; G01N 33/566; C12Q 1/34; C12N 9/96
[52] U.S. Cl. ............ 435/7.1; 435/19; 435/18; 435/188; 436/71
[58] Field of Search ............ 435/7.1, 11, 19, 18; 436/71

[56] References Cited

U.S. PATENT DOCUMENTS

| | | | |
|---|---|---|---|
| 3,983,005 | 9/1976 | Goodhue et al. | 435/11 |
| 4,195,126 | 3/1980 | Hall | 435/11 |
| 4,241,178 | 12/1980 | Esders et al. | 435/15 |
| 4,839,298 | 6/1989 | Kay et al. | 436/175 |
| 4,945,146 | 6/1990 | Kapmeyer et al. | 526/304 |

FOREIGN PATENT DOCUMENTS

WO91/04338 4/1991 WIPO .

OTHER PUBLICATIONS

Zubay, G. Biochemistry. Reading, Mass.:Addison-Wesley Publishing Co., 1983 pp. 478–479.
Wilton, D. C. Studies on fatty-acid-binding proteins, The purification of rat liver fatty acid binding protein and the role of cysteine-69 in fatty acid binding, Biochemical Journal 261:273–276, 1989.
Windholz, M; ed, The Merck Index, 10th edition Rahway, N.J.: Merck and Co., Inc. 1983. p. 671.
Vincent S. H. et al. A protein of the Z class of liver cytosolic proteins in the Rat that Preferentially binds Heme. Journal of Biological Chemistry 260(27):14521–14528, 1985.
Ransom, J. P. Practical Competitive binding assay methods. St. Louis: C. V. Mosby Co., 1976, Chapters 1 & 4, pp. 2–9 & 42–53.
D. C. Wilton. "A continuous fluorescence displacement . . . " Biochemical Journal, vol. 266 No. 2, (Mar. 1990) London, pp. 435–439.
D. C. Wilton. "The fatty acid analogue 11- . . . " Biochemical Journal, vol. 270 No. 1 (15 Aug. 1990), London, pp. 163–166.

Primary Examiner—Toni R. Scheiner
Assistant Examiner—Nancy Parsons
Attorney, Agent, or Firm—Nixon & Vanderhye

[57] ABSTRACT

A method of quantitative assay for a substrate such as triglyceride capable of undergoing enzymatic hydrolysis to release long chain fatty acids in an albumin-containing clinical sample comprises incubating the albumin-containing clinical sample with an enzyme such as lipase which acts upon the substrate to be assayed under conditions effective to release fatty acid therefrom, causing the fatty acid thus released to bind to a fatty acid binding protein (FABP) and assaying the binding of the fatty acid to the FABP.

10 Claims, 2 Drawing Sheets

ASSAY FOR THE QUANTITATIVE DETERMINATION OF SUBSTRATES CAPABLE OF UNDERGOING ENZYMATIC HYDROLYSIS TO RELEASE LONG-CHAIN FATTY ACIDS

BACKGROUND OF THE INVENTION

1. Field of the Invention

This invention relates to a quantitative assay, applicable to clinical samples, for substrates which can undergo enzymatic hydrolysis to release long chain fatty acids. The invention is particularly, though not exclusively, directed to ester substrates such as the triglyceride substrates for lipase and phospholipid substrates for the phospholipases.

2. Description of the Prior Art

Esters such as the tri and diglycerides are ubiquitous and fundamental to every aspect of cell membrane function and energy transfer. The assay of these components is therefore of interest in many areas of clinical diagnosis. Thus, for example, assay of the triglyceride content of a clinical specimen can give some indication of recent dietary fat intake, and the ability of the liver to metabolise fats for energy utilisation. However presently available methods for assay of triglycerides, such as those available commercially as Kits from the Sigma Chemical Co. Ltd. (Poole, Dorset, UK) rely on the measurement of glycerol released by enzyme hydrolysis. Thus, in Sigma procedure no. 405, triglycerides are extracted into isopropanol and saponified with potassium hydroxide. Liberated glycerol is then converted to formaldehyde by periodate. By reacting with acetylacetone, the formaldehyde forms yellow diacetyldihydrolutidine, which is measured colorimetrically.

In Sigma procedures nos. 336, 337, 339 and 334 glycerol is released from triglyceride enzymatically using lipase, and glycerol is further reacted with ATP to form glycerol-1-phosphate. The four methods then differ only in the way by which the glycerol-1-phosphate is further reacted to produce a change in absorbance which can be measured spectrophotometrically. Such assays, when applied to clinical samples, suffer from the disadvantage that as glycerol itself is a product of cell metabolism, assay of the glycerol content of a blood specimen may not give an accurate picture of the circulating triglyceride levels in the subject (see Cole, Clin. Chem. 36/7, 1267–1268 (1990)). There is clearly a need for the development of alternative means for assaying triglycerides and other related substrates, such as phospholipids and cholesterol esters, that give accurate results at low concentrations or in small clinical blood specimens.

SUMMARY OF THE INVENTION

It has now been found that such substrates can be quantitatively assayed in albumin-containing clinical samples, such as serum, rapidly and sensitively by causing the appropriate enzyme to act on the substrate to release fatty acid(s), and then detecting or measuring the binding of the released fatty acids to a protein which binds fatty acids with high affinity (having a dissociation constant of $10^{-5}M$ or less). Such a protein is very desirably that known as fatty acid binding protein (FABP), which is a natural product extractable, for example, from the liver of animals. Hereinafter the invention is described with reference to FABP but it will be understood that other binding proteins of the kind described could be substituted for FABP. In addition, the invention is described with reference to serum as the clinical specimen, although it will be understood that the invention is applicable to other clinical specimens such as whole blood and plasma as well as to partially-purified fractions derived from these. The assay of the fatty acid-FABP binding interaction is most conveniently carried out by using a labelled probe, in effect a labelled fatty acid, which competes with the fatty acid released by the action of lipase for binding sites on the FABP. Conveniently the amount of free label, i.e. that which is not bound to the FABP, is then measured.

It was to be expected from the observations of the prior art that the albumin present in such clinical specimens would interfere with the effectiveness of the assay unless removed. Thus earlier findings given in Biochem. J. (1990), 266, 435–439 and Biochem. J. (1990), 270, 163–166 indicate that serum albumin has sites capable of binding with fatty acids. Surprisingly however, it has been found that the substrate assay of the invention is of sufficiently high sensitivity to obviate the need for prior removal of competing protein such as albumin. It was also surprising that the enzyme based substrate assay of the invention reaches completion and does so sufficiently rapidly to permit quantitative determination of the amount of substrate present.

Accordingly, embodying the above-stated principles, there is provided a method of quantitative assay for a substrate capable of undergoing enzymatic hydrolysis to release long chain fatty acids in an albumin-containing clinical sample which comprises incubating the albumin-containing clinical sample with an enzyme which acts upon the substrate to be assayed under conditions effective to release fatty acid therefrom, causing the fatty acid thus released to bind to a fatty acid binding protein (FABP) and assaying the binding of the fatty acid to the FABP.

The invention also includes a kit for carrying out an assay of the invention, the kit comprising fatty acid binding protein (FABP) and an enzyme capable of hydrolysing the substrate being assayed to release long chain fatty acid. Preferably a labelled probe which binds to the FABP competition with the fatty acid is included in the kit.

DESCRIPTION OF THE PREFERRED EMBODIMENTS

The assay of the invention is applicable in principle to the serum of any mammal, but is, of course, mainly of interest in relation to humans.

An important further purpose of the invention is to detect and/or monitor the concentration of triglycerides In the blood. The assay is also applicable, for example, to the assay of cholesterol esters in albumin-containing serum using an appropriate cholesterol esterase and to the assay of phospholipids using phospholipase A2.

Because of the possibility of albumin exerting a competing role in the assay, it would, as explained above, appear normally necessary to remove it. However, due to the high sensitivity of the assay, this has been found to be unnecessary. Preferably the clinical sample is of 1 $\mu l$ or less, suitably 0.1 to 1 $\mu l$, in order to minimise any effect of the albumin.

The albumin-containing serum sample is incubated with the enzyme at any temperature effective for the enzymatic hydrolysis to occur. Most conveniently room temperature (20-25° C.) is used, but temperatures of from 15° to 40° C. are normally operable.

It will be understood that it is the appropriate enzyme which is added in the second step of the assay. Thus excess lipase can be used to assay the amount of triglyceride in the assay sample. Cholesterol esterase can be employed in the assay of cholesterol esters. Phospholipase A2 can be employed in the assay of phospholipids.

The fatty acid binding protein (FABP) is also added to the incubation mixture before, during or after introduction of the enzyme. There are various types of FABP operable. They are preferably cytosolic and are normally designated by the tissue from which they were isolated, e.g. small intestine, heart muscle, liver and adipose tissue. Hepatic FABP is preferred and is conveniently extracted from the liver of animals, for example from rats, pigs or bovines. A preferred extraction procedure is that described by D. C. Wilton, Biochem J. 261, 273-276 (1989). The FABP need not be a natural product. It can be a synthetic analogue which binds acids or it may be the analogue of a natural product obtained by a recombinant DNA method, e.g. the rat liver FABP produced by expression of the gene in E. coli, see J. B. Lowe et al., J. Biol. Chem. 259, 12696-12704 (1984) and A. F. Worrall et al., Biochem. J., 278, 365-368, 1991. Any incubation conditions effective to bind the acid released by the lipase can be used. Broadly, the same temperatures as in the hydrolysis step are operable.

It is also necessary to detect that acid-FABP binding has taken place. The preferred means of doing this is by a competition assay in which a competitive fatty acid species is caused to compete with the fatty acid released by the enzyme for a limited number of binding sites on the FABP. The competitive species is herein called a "probe". It may comprise a label portion and long chain aliphatic portion, connected to an acid group and typically having from 9 to 19 carbon atoms excluding the acid group. The label portion can be a fluorophore, chromophore or luminophore, for example. Radiolabels are less preferred.

In one preferred embodiment, the label is a polycyclic fluorophore, especially a naphthalene or anthracene having a polarity-sensitive fluorescent group. A polarity-sensitive fluorescent group is one which undergoes a change in its fluorescence emission (quantum yield and wavelength maximum) as it moves from a polar to non-polar environment. A large change in fluorescence signal at a fixed wavelength is observable as the probe moves to a polar micro-environment (the assay medium which will normally be aqueous) from the non-polar micro-environment of the FABP molecule. The probe is negatively charged and is therefore normally present as an acid salt. Particularly preferred such probes are those of formula Pc—Z—NH—$(CH_2)_n$—X$^-$ wherein:

Pc represents a naphthalene or anthracene residue;

Z represents —CO— or —$SO_2$—; and

X$^-$ represents the anion of an acid group, preferably COO$^-$.

n is from 4 to 24, preferably 8 to 19, especially 8 to 12.

Salts of 11-(dansylamino)undecanoic acid (DAUDA) of formula

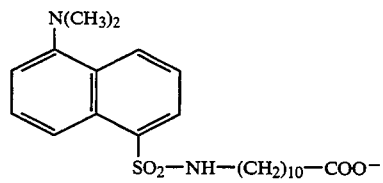

are particularly preferred. This probe is Known to bind to FABP in competition with fatty acids, see T. C. I. Wilkinson and D. C. Wilton, Biochem. J. 247, 485-488 (1987). However, it was surprising to find that when employed in combination with a system including a substrate and an enzyme capable of hydrolysing the substrate to release long chain fatty acid, a complete and rapid reaction occurred which could be quantitatively assayed by observing the change in fluorescence signal. Other fluorophores which can be used are 9-anthroyloxy fatty acids see J. Storch et al., J. Biol. Chem 264, 8708-8713 (1989), and cis-parinaric acid (a polyene fatty acid), see H. J. K. Keuper et al., Chem. Phys. Lipids 38, 159-178 (1985). Alternatively a colorimetric probe such as hemin can be employed. Such a molecule also binds to FABP in competition with the fatty acid released by the enzyme and change in colour can be assayed spectrophotometrically. Other chromophores which can be used include bilirubin.

Alternatively the "probe" need not in itself comprise a label portion and may be indirectly assayed. Instead the probe may itself act as an enhancer, inhibitor, cofactor or other trigger capable of modulating a suitable indicator reaction on displacement from the FABP.

A further alternative assay comprises adding to the assay medium a labelled acid, e.g. $^{14}C$ or $^3H$ radiolabelled, or one to which a chromophore has been attached, and measuring the amount of labelled acid remaining in solution after competition between the acid released by the lipase and the labelled acid for a limited amount of FABP. The labelled acid can be measured by insolubilising it on Lipidex 1000, see J. F. C. Glatz and J. H. VeerKamp, Anal. Biochem 132, 89-95 (1983), separating the Lipidex 1000 from the assay medium and determining the amount of labelled material thereon.

The competition assay species can be added to the assay mixture before, simultaneously with or after the fatty acid and before or after addition of the enzyme. The assay is regarded as "competitive", when one species displaces the other from the FABP to attain an equilibrum position for the reversible binding reaction. When the competing species binds to the FABP, the binding can be measured in various ways. In the case of a polarity-sensitive fluorophore, the change in fluorescence is easily monitored. Changes in the colour and intensity of a chromophore or of intensity of a luminophore are also susceptible to measurement. Alternatively, it is possible to precipitate the FABP-probe species, separate the precipitate, and measure the amount of label bound to the FABP or the amount of free label remaining in solution. This could be done by means of an immobilised antibody to the FABP, for example, or by coupling the FABP directly to an insoluble material such as agarose.

In an alternative procedure, the fatty acid ester is labelled in the acid moiety, e.g. by bonding it to a fluorescent reporter group and the amount of binding of the released fluorescent fatty acid to the FABP measured by a suitable spectral change occurring upon binding.

BRIEF DESCRIPTION OF THE DRAWINGS

The invention will now be further described in relation to the accompanying drawings, in which.

EXAMPLES

The following Examples illustrate the invention.

Example 1

A solution of buffer containing substrate and the fluorescent probe was prepared as follows:

To 20 ml of 0.1M Tris buffer pH 8.0 containing 0.1M NaCl in a Sterilin tube was added 0.05 ml of 11-(dansylamino)undecanoic acid (DAUDA) (0.38 mM) in methanol. The mixture was briefly shaken. 2 ml of this assay solution was added to a 4 ml plastic disposable fluorimeter cuvette, which was then placed in a Perkin-Elmer LS 3B fluorimeter at room temperature. The excitation wavelength was 350 nm and the fluorescence was measured at 500 nm. The machine was zeroed to give no fluorescence reading. 0.02 ml of a 70% saturated ammonium sulphate supernatant of an *E. coli* lysate containing recombinant rat liver FABP (1 mg/ml), derived from the expression of a synthetic gene for this protein, was added.

0.02 ml of a serum sample (obtained from the Pathology Laboratory, Southampton General Hospital) was diluted to 1 ml with distilled water containing 0.1% of the non-ionic detergent Triton X-100. 0.01 ml of this diluted serum sample was added to the assay mixture. The fluorimeter sensitivity was set to give a reading of about 90% on the chart recorder and the initial reading noted.

Excess lipase (0.005 ml) from Rhizopus arrhizus was added (6250 Units). A rapid fall in fluorescence was noted within 30 seconds at room temperature and this value was noted, although the reaction was monitored over a 1–2 minute incubation period, during which a slower fall in fluorescence was noted (believed to be due to hydrolysis of the 2-monoglyceride product of the primary hydrolysis). Calibration may be achieved by titrating oleic acid into the complete assay mixture in the absence of lipase or, more conveniently, by using serum samples of predetermined triglyceride concentration.

Figure 1:
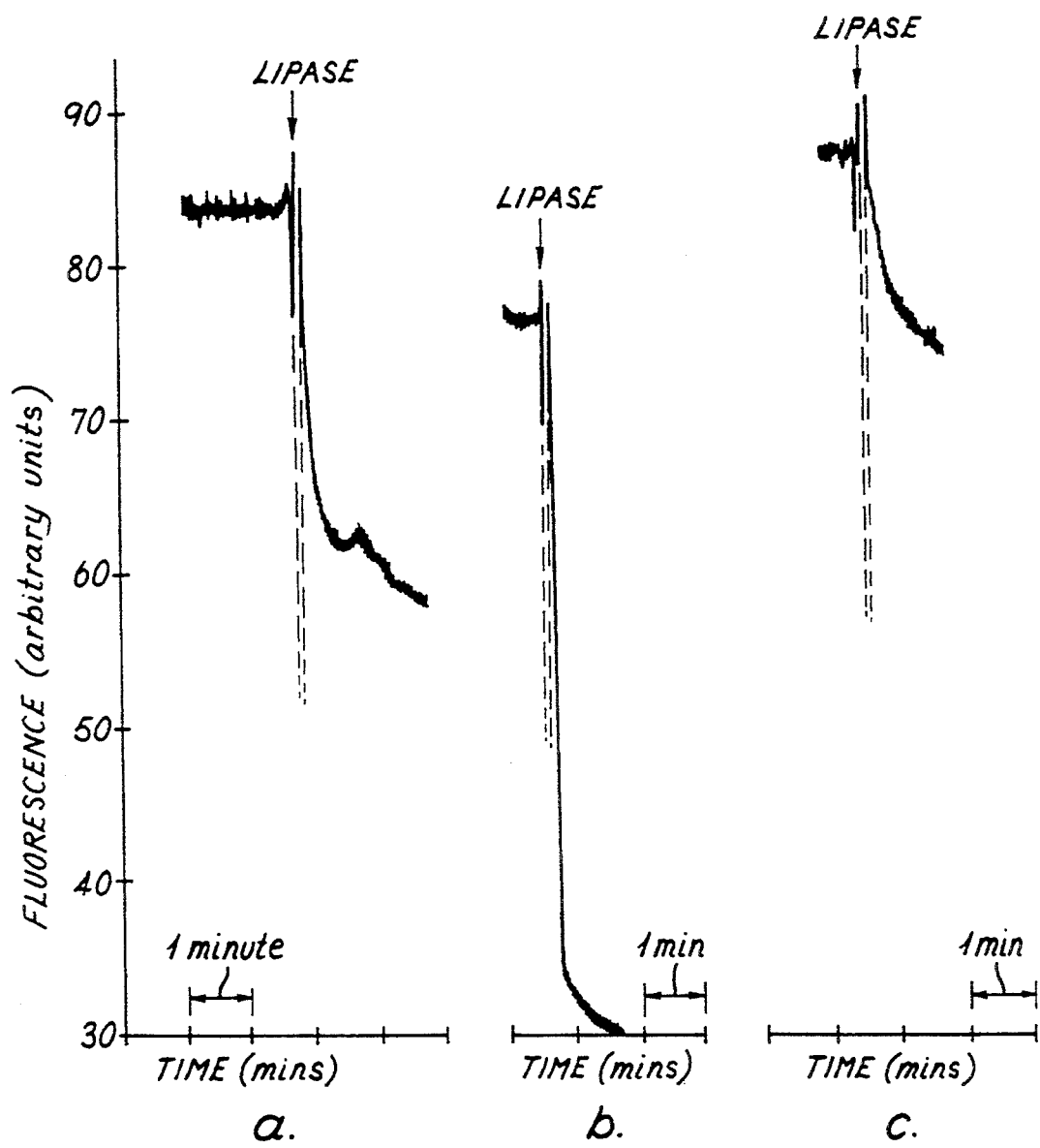
FIGS. 1 (a–c) shows fluorescence displacement traces for three serum samples (a), (b) and (c)

FIG. 1 shows the fluorescence displacement traces for three serum samples a), b) and c). The change in fluorescence after 30 seconds was measured in each case and, as can be seen, these changes ($\Delta F$) are for a) 22 units, b) 47 units and c) 10 units.

Using sample a) (reported by the source as having 3.7 mM triglyceride) for calibration, this corresponds to triglyceride values for a) 3.7 mM, b) 8–9 mM and c) 1.68 mM.

Example 2

To 1 ml of 0.1M Tris buffer pH 8.0 containing 0.1M NaCl in a plastic spectrophotometer cuvette was added 0.01 ml of 0.4 mM haem in 0.04M ammonium hydroxide. An identical blank cuvette was also prepared and these two cuvettes were zeroed at 405 nm to give no absorbance in an Hitachi U2000 spectrophotometer. 0.05 ml of 70% saturated ammonium sulphate supernatant of an *E. coli* lysate containing recombinant FABP (1 mg/ml) derived from the expression of a synthetic gene for this protein was added to the reaction cuvette and similar volume of water to the blank. The enhanced absorbance at 405 nm due to haem binding to FABP was recorded. 0.01 ml of diluted serum (equivalent to 0.2 μl of serum) was added to the reaction and after recording the absorbance, excess lipase (0.005 ml) from Rhizopus arrhizus was added (6250 Units). The fall in absorbance at 405 nm was monitored over a 1–2 minute period.

Figure 2:
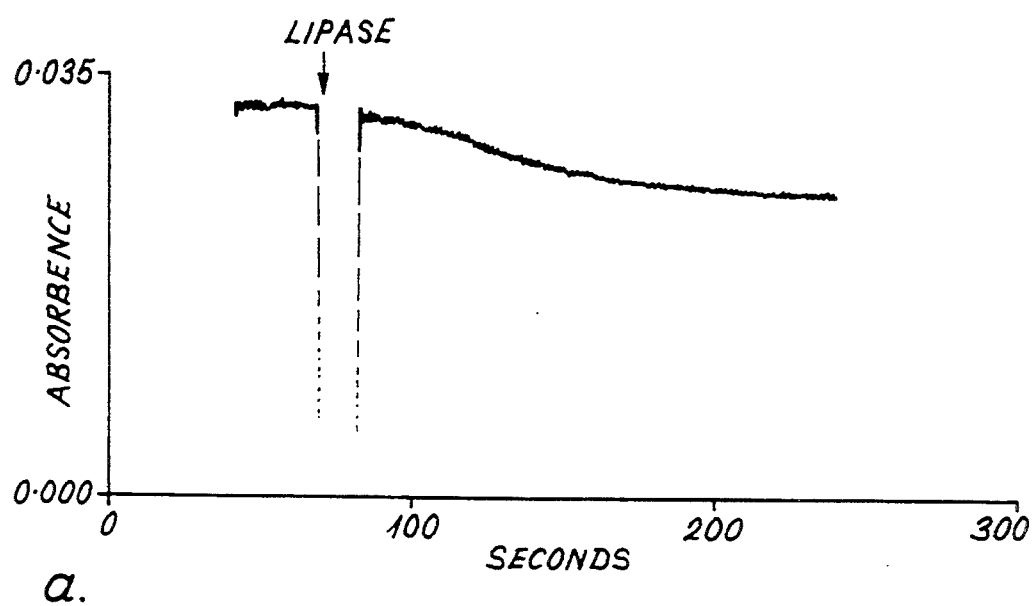
FIGS. 2 (a–b) shows absorbance displacement traces for two serum samples (a) and (b).
Figure 2:
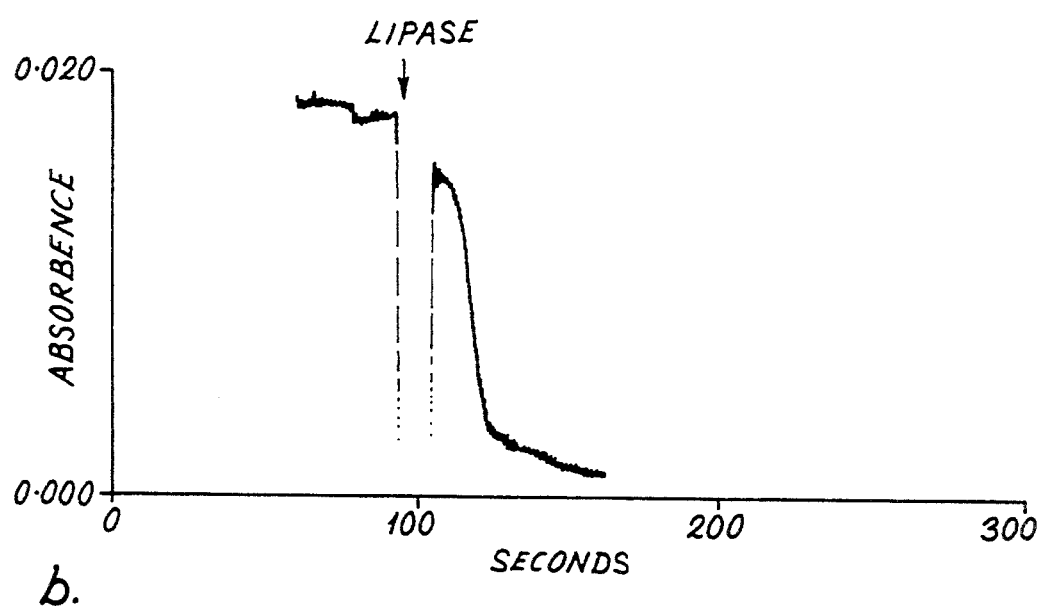

FIG. 2 shows the absorbance displacement traces for two serum samples a) and b) having triglyceride concentrations of 3.7 mM and 11.9 mM respectively. The change in absorbance after 30 seconds was measured in each case and, as can be seen, these changes ($\Delta ABS$) are for a) 0.006 and for b) 0.016.

I claim:

1. A method for assaying a substrate present in an albumin-containing clinical sample which substrate can be enzymatically hydrolyzed to release long chain fatty acids therefrom, said method comprising the steps of:
   (i) adding to said clinical sample an enzyme which releases fatty acids from said substrate, to form an incubation mixture;
   (ii) incubating said incubation mixture;
   (iii) adding to said incubation mixture before, during or after step (ii) fatty acid binding protein (FABP); and
   (iv) measuring binding of said released fatty acids to said FABP.

2. The method according to claim 1 wherein the FABP is measuring by a method in which a competitive probe which binds to the FABP in competition with the released fatty acids is allowed to interact with the FABP and the free or bound competitive probe is then measuring directly or indirectly.

3. The method according to claim 2 wherein the probe is measuring by fluorescence displacement.

4. The method according to claim 3 wherein the probe is an anion of 11-(dansylamino)undecanoic acid.

5. The method according to claim 2 wherein the probe is measuring colorimetrically.

6. The method according to claim 5 wherein the probe is hemin.

7. The method according to claim 1 for assaying triglycerides wherein the enzyme is lipase.

8. The method according to claim 1 wherein the FABP is hepatic.

9. The method according to claim 1 wherein the clinical sample is a serum sample.

10. The method according to claim 1 wherein the clinical sample is 0.1 to 1 μl.

* * * * *